United States Patent [19]

Hashimoto

[11] Patent Number: 5,309,214
[45] Date of Patent: May 3, 1994

[54] METHOD FOR MEASURING DISTRIBUTED DISPERSION OF GRADIENT-INDEX OPTICAL ELEMENTS AND OPTICAL SYSTEM TO BE USED FOR CARRYING OUT THE METHOD

[75] Inventor: Takeshi Hashimoto, Fussa, Japan

[73] Assignee: Olympus Optical Co., Ltd., Tokyo, Japan

[21] Appl. No.: 945,612

[22] Filed: Sep. 16, 1992

[30] Foreign Application Priority Data

Sep. 17, 1991 [JP] Japan ............................ 3-236289
May 29, 1992 [JP] Japan ............................ 4-138670

[51] Int. Cl.$^5$ ........................................ G01N 21/43
[52] U.S. Cl. ............................ 356/128; 356/73.1; 356/136
[58] Field of Search ............... 356/73.1, 128, 135, 356/136

[56] References Cited

FOREIGN PATENT DOCUMENTS 63-275936 11/1988 Japan .
88937 3/1990 Japan ............................ 356/73.1

OTHER PUBLICATIONS

Zhu et al; "Scanning Total Reflection Method for Refractive-Index Profiling" Japanese Journal of Applied Physics, vol. 28, No. 8, Aug. 1989, pp. 1497–1500.

Primary Examiner—F. L. Evans
Attorney, Agent, or Firm—Cushman, Darby & Cushman

[57] ABSTRACT

A method for measuring a refractive index profile and distributed dispersion of a sample by measuring refractive indices at a plurality of wavelengths at measuring points on the sample and calculating a refractive index profile at a main wavelength of the sample from the measured refractive indices. A condenser optical system for carrying out this method comprises a converging optical system for converging light beams emitted from light sources, a stop for shaping a wave front, a collimator optical system for transforming light beams having passed through the stop into parallel light beams, a relay lens system for converging these light beams and returning these light beams again to parallel light beams, an alignment stop disposed at a location of a parfocal point of the relay lens system, a condenser lens system for focusing light beams having passed through the relay lens system onto the measuring points, a light beam splitter means allowing light beams travelling toward the measuring points to pass therethrough and reflecting light beams returned from the measuring points, a photodetector for receiving light beams split by the light beam splitter means, and an alignment optical system having an alignment mechanism for aligning the light beams by using outputs from the photodetector.

5 Claims, 6 Drawing Sheets

METHOD FOR MEASURING DISTRIBUTED DISPERSION OF GRADIENT-INDEX OPTICAL ELEMENTS AND OPTICAL SYSTEM TO BE USED FOR CARRYING OUT THE METHOD

BACKGROUND OF THE INVENTION a) Field of the Invention

The present invention relates to a method for measuring distributed dispersion of gradient-index optical elements and an optical system to be used for carrying out the method.

b) Description of the Prior Art:

In the recent years, gradient-index optical elements have been used increasingly as pickups for video disks and copying machines. Further, relatively small gradient-index optical elements such as optical wave guides and planar microlenses are being put to practical use in a field of opto-electronics, whereas gradient-index optical elements having relatively large diameters are being adopted in lens systems for cameras using silver salt diffusion transfer process, video cameras and microscopes and so on in a field of image processing.

Since these gradient-index optical elements have characteristics which are largely variable dependently on refractive index profiles thereof, it is necessary for practical use of these gradient-index optical elements to measure data on the refractive index profiles of the gradient-index optical elements with high accuracy.

When a gradient-index optical element is to be adopted in the field of opto-electronics wherein the optical element is to be used mainly at a single wavelength, it is sufficient to measure a refractive index profile only at the intended wavelength. When a gradient-index optical element is to be adopted in the field of image processing wherein the optical element is to be used mainly within a broad wavelength region, in contrast, it is necessary to accurately measure a refractive index profile and distributed dispersion at a main wavelength (a wavelength selected as a standard).

Under the present circumstance, there has been proposed no method yet for measuring accurately and directly distributed dispersion of a gradient-index optical element, but it is known to those skilled in the art that distributed dispersion can be determined from refractive index profiles measured at a plurality of wavelengths. Accordingly, methods for measuring refractive index profiles will be described below as the prior art.

As the conventional methods for measuring refractive index profiles, there are known the longitudinal interference method which permits determining refractive index profiles by observing, through an interference microscope, thin samples sliced and polished in a direction perpendicular to center axes of the refractive index profiles, and by calculating optical path differences per unit thickness of the thin samples, as well as the traverse interference method which permits determining refractive index profiles by tracing rays while allowing the rays in directions perpendicular to the center axes of the refractive index profiles of cylindrical samples to be measured.

More recently, Japanese Patent Preliminary Publication No. Sho 63-275936 has proposed another method for measuring refractive index profiles. The principle of Pülfrich refractometer, which is well known to those skilled in the art, is applied to this method. A system for carrying out this method is illustrated in FIG. 1, wherein a sample 101 which is to be subjected to the measurement of a refractive index profile is mounted on a hemispherical sample stage 102 so that a measuring surface of the sample 101 is in close contract with a sample mounting surface 102A of the sample stage 102, and a laser beam 105 is focused by a condenser lens 103 onto a measuring point 104 on the mounting surface 102A through a hemispherical surface 102B other than the sample mounting surface 102A. Since light beams which are allowed to be incident on the measuring point 104 within a range of angles of incidence larger than a critical angle of total reflection $\phi_c$ are totally reflected, reflected light beams having brightness nearly equal to the incident light beams are obtained within a region of 106, whereas most of light beams which are allowed to be incident on the measuring point 104 within another range of angles of incidence smaller than the critical angle $\phi_c$ transmit outside through the measuring point 104 and reflected light beams having brightness lower than that of the incident light beams are obtained within another region 107. By measuring a light bundle which is reflected by the measuring point 104, it is therefore possible to measure a section 109 of the light bundle on which the relatively bright region 106 and the relatively dark region 107 are formed on both sides of a bright-dark boundary 108. Since a ray which is allowed to be incident on the measuring point 104 at the critical angle $\phi_c$ of total reflection is reflected to the boundary 108 located between the bright region and the dark region, it is possible to determine the critical angle of total reflection by measuring an angle of the boundary between the bright and dark regions relative to a normal to the measuring surface, and calculate a refractive index n of the sample 101 at the measuring point 104 from a known refractive index of the sample stage by using the following formula (1):

$$n = n_o \sin \phi_c \qquad (1).$$

Furthermore, it is possible to measure a refractive index profile of the sample 101 by displacing the sample 101 in the horizontal direction while it is kept in close contact with the sample stage 102.

Since dispersion at each point of the sample 101 is calculated from refractive indices which are measured in absolute at a plurality of wavelengths, determination of distributed dispersion by utilizing the conventional methods for measuring refractive index profiles poses problems that refractive indices of one and the same position of a sample at a plurality of wavelengths must be selected accurately, after measurements and that errors involved in data obtained by measurements inevitably produce large influence on determination of the distributed dispersion. As a result, it is obliged to adopt, for determining distributed dispersion with high accuracy, complicated and expensive members for obtaining position data.

Moreover, the longitudinal and traverse interference methods measure refractive index differences, i.e., relative refractive index profiles with high accuracies, but do not allow to determine dispersion directly from the data obtained by the measurements at the plurality of wavelengths. These method do not permit determining distributed dispersion without using refractive indices measured in absolute values by another method at the same positions and at the plurality of wavelength in combination with the refractive index profiles measured by the longitudinal or traverse interference method.

In addition, the method proposed by Japanese Patent Preliminary Publication No. Sho 63-275936 is intended to be applied only to the field of opto-electronics, adapted to measure a refractive index profile at a single wavelength and therefore insufficient for accurate determination of distributed dispersion by the measurements of refractive index profiles at a plurality of wavelengths.

SUMMARY OF THE INVENTION

A primary object of the present invention is to provide a method and an optical system for measuring distributed dispersion of optical elements.

According to the present invention, this object can be attained by configuring the method so as to comprise a step to bring a medium member having a refractive index higher than that of a sample to be measured into contact with one surface of the sample, a step to allow plural types of light beams having a plurality of wavelengths different from one another and traveling along one and the same optical axis to be incident as converging light beams onto measuring points on the surface through the medium member, a step to detect, as critical angles of total reflection, boundaries between bright and dark regions formed by light beams reflected from the measuring points, a step to measure refractive indices of the sample at the measuring points at the plurality of wavelengths, a step to calculate dispersion at the measuring points on the sample from the critical angles of total reflection and the refractive indices, and a step to calculate distributed dispersion of the sample by repeating the steps described above while shifting the sample.

In a preferred formation of the method according to the present invention, the method comprises a step to determine refractive indices and dispersion of the sample at a main wavelength from values measured at the measuring points at the plurality of wavelengths.

Since the method according to the present invention is adapted so as to allow measuring light beams having a plurality of wavelengths to be incident on the sample along one and the same optical axis, this method permits determining distributed dispersion of gradient-index optical elements.

The optical system for carrying out the method according to the present invention comprises light source means for emitting light beams having wavelengths different from one another so as to travel along an optical axis, a collimator optical system for transforming the light beams emitted from the light source means into parallel light beams, a sample mounting member which is nearly hemispherical, transparent for the light beams emitted from the light source means and has a flat surface for mounting the sample thereon, a condenser optical system for converging the parallel light beams onto areas located in the vicinity of the center of sphere of the sample mounting member, a measuring means for detecting light beams reflected by the sample, a means for calculating dispersion at the measuring points on the sample on the basis of outputs provided from the measuring means, and a scanning means for shifting the sample along the surface of the sample mounting member.

In a preferred formation of the optical system according to the present invention, the collimator optical system comprises a converging optical component, a stop disposed on an optical axis of light beams having passed through the stop, a collimator optical component for transforming light beams having passed through the stop into parallel light beams, a relay lens system including a first lens system for converging parallel light beams having passed through the collimator optical component and a second lens system disposed so as to have a focal point coincident with that of the first lens system, an alignment stop disposed at the location of the focal point common to the first lens system and the second lens system, a light beam splitter means which is disposed on the incidence side of the alignment stop and functions to split light beams reflected and returned by the spherical surface of the sample mounting member, and a photodetector means disposed on an optical axis of light beams split by the light beam splitter means.

Since the optical system according to the present invention can focus measuring light beams accurately and easily on the measuring points, the optical system makes it possible to measure distributed dispersion of samples with high accuracy.

These and other objects as well as the features and the advantages of the present invention will become apparent from the following detailed description of the preferred embodiments when taken in conjunction with the accompanying drawings.

DESCRIPTION OF THE PREFERRED EMBODIMENTS

Figure 2:
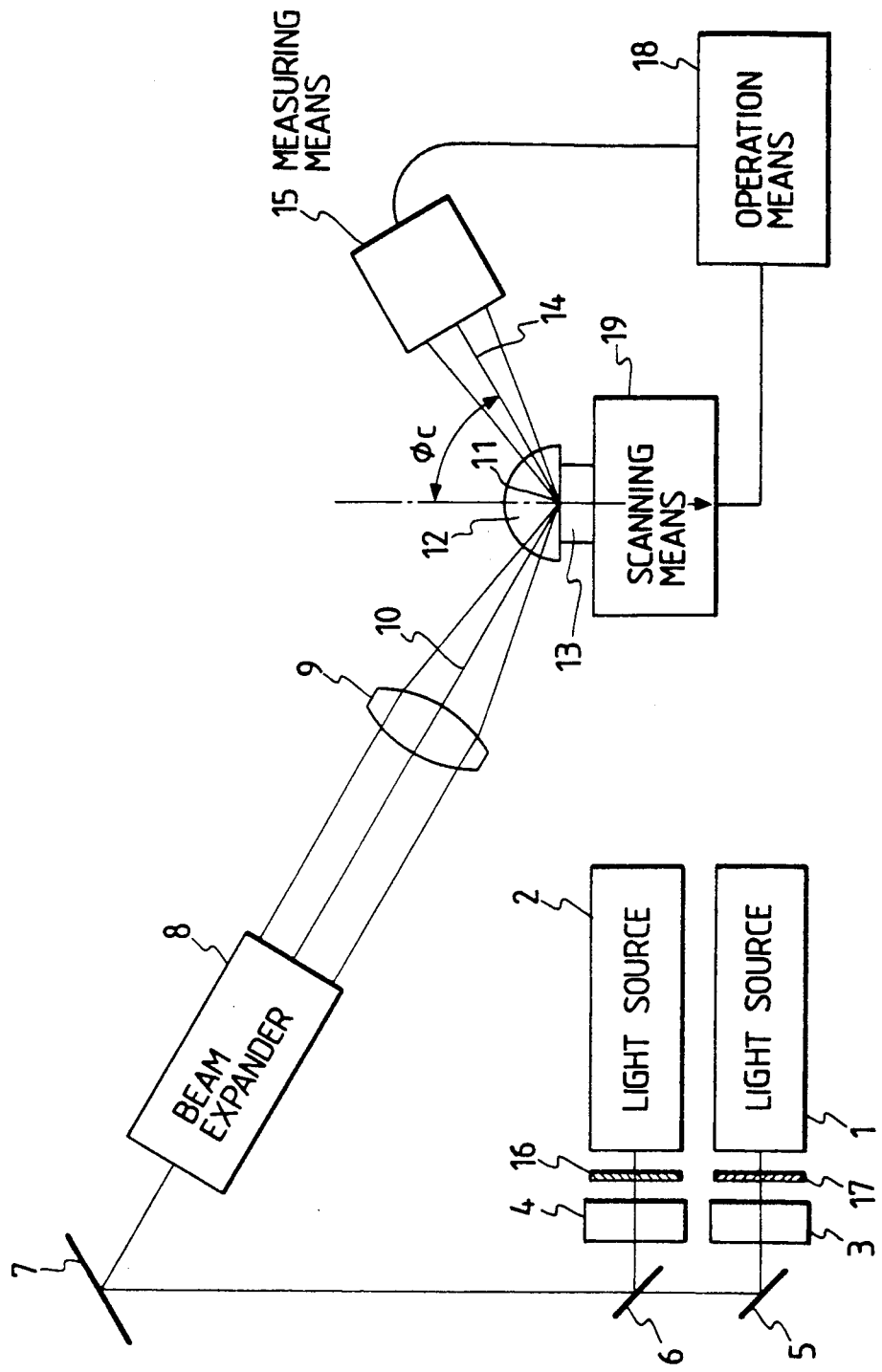
FIG. 2 is a sectional view descriptive of the principle of an embodiment of the distributed dispersion measuring method according to the present invention.

FIG. 2 illustrates an optical system which is to be used for measuring the gradient of dispersion by the method according to the present invention. In this drawing, the reference numeral 1 represents a light source for emitting He-Ne laser having a wavelength of 632.8 nm, the reference numeral 2 designates another light source for emitting Ar laser having a wavelength of 488 nm. The lasers which are emitted from these light sources can be controlled so as to have optical axes coincident with each other by parallel plates 3 and 4 having controlling means (not shown) respectively, a mirror 5 having a controlling means (not shown), a beam splitter 6 having a controlling means (not shown) and controlling means (not shown) arranged in the light sources. The reference numeral 7 denotes a mirror which has a controlling means (not shown) and functions to reflect toward a measuring point 11 the lasers having optical axes coincident with each other. The lasers which are reflected by the mirror 7 are expanded into laser beams having diameter approximately 10 times as large as an original diameter of the laser beams by a beam expander 8 and converted into converging beams by an objective lens 9 which has a magnification of 10× and a long working distance (a distance as measured from the lens to the measuring point 11) so that these laser beams can be focused onto the measuring point 11 by using a controlling means (not shown) which is capable of displacing the objective lens 9 in the direction along the optical axis and the direction perpendicular to the optical axis.

The reference numeral 12 represents a medium member. This medium member is configured so as to have, for example, a spherical surface having a radius of r=20 mm on the side on which the incident laser beam 10 is to be incident and a nearly planar surface on the side on which a sample is to be mounted. This medium member is made, for example, of a glass material which exhibits a refractive index of 1.69426 for the He-Ne laser and an Abbe's number of 30.1. The measuring point 11 is located at the center of the sphere of the medium member 12 which is located on a measuring surface of a sample 13 and corresponds to an ideal point on which the incident laser beam is to be focused.

The sample 13 is an optical element and is kept in contact with the medium member 12 which is coated with a matching liquid exhibiting a refractive index of 1.6931 for the He-Ne laser. The refractive indices of the medium member 12 and the matching liquid are both higher than that of the sample 13.

The reference numeral 14 designates a laser beam which is reflected by the measuring surface and the reference numeral 15 denotes a measuring means. The measuring means 15 is disposed at a location which is approximately 50 mm apart from the measuring point, i.e., the center of the sphere of the medium member 12, equipped with a photodetector rotatable around the center 11 of the sphere, adopted for measuring a critical angle of total reflection while receiving the reflected laser beam 14, and capable of measuring, as a critical angle $\phi_c$ of total reflection, a location at which intensity of the received electromagnetic wave changes most abruptly, i.e., and angle formed between a bright-dark boundary in the reflected laser beam 14 and a normal to the measuring surface on the medium member 12. The measurement of the distributed dispersion is performed by measuring critical angles $\phi_c$ of total reflection of the He-Ne laser beam emitted from the light source 1 and the Ar laser beam emitted from the light source 2 respectively while irradiating the measuring point 11 alternately with these laser beams by using shutters 16 and 17, and refractive indices of the sample 13 at the measuring point by an operation means 18 according to the formula (1) mentioned above. The reference numeral 19 represents a scanning means which is adopted for scanning the sample 13 in two dimension along a flat surface of the medium member 12 and is capable of detecting a location of the measuring point while fixing the measuring point at a location.

The operation means has functions to calculate refractive indices by using the critical angles of total reflection at wavelengths measured by the measuring means 15 each time the measuring point is displaced by the scanning means 19, calculate refractive indices and dispersion (Abbe's numbers) at a main wavelength from the refractive indices at the above-mentioned wavelengths, and simultaneously calculate and output refractive index profiles and distributed dispersion at the main wavelength while receiving measured position data from the scanning means 19.

The table shown below exemplifies measuring results of a refractive index profile and distributed dispersion at a main wavelength of a gradient-index planar lens having a small diameter which are measured by the method for measuring distributed dispersion according to the present invention. For these measurements, a scanning direction was selected in the diametrical direction of the sample 13 for simplicity. The main wavelength was selected at the wavelength of the d-line (587.56 nm) which is used as a standard for designing optical systems to be used in the visible region and dispersion is calculated as an Abbe's number $\nu_d$ for the d-line.

TABLE 1

| Distance from one edge of hemispherical lens (mm) | Refractive index for He—Ne laser (632.8 nm) | Refractive index for Ar laser (488 nm) | Refractive index at main wavelength (587.56 nm) | Dispersion (Abbe's number) at main wavelength (587.56 nm) |
|---|---|---|---|---|
| 0.05 | 1.56978 | 1.58120 | 1.57242 | 44.71 |
| 0.10 | 1.57411 | 1.58601 | 1.57686 | 43.25 |
| 0.15 | 1.57833 | 1.59047 | 1.58113 | 42.71 |
| 0.20 | 1.58235 | 1.59474 | 1.58520 | 42.15 |
| 0.40 | 1.59683 | 1.61030 | 1.59992 | 39.78 |
| 0.60 | 1.60927 | 1.62374 | 1.61258 | 37.79 |
| 0.80 | 1.61970 | 1.63503 | 1.62320 | 36.30 |
| 1.00 | 1.62813 | 1.64430 | 1.63181 | 34.90 |
| 1.20 | 1.63492 | 1.65160 | 1.63872 | 34.22 |
| 1.40 | 1.64007 | 1.65732 | 1.64399 | 33.36 |
| 1.60 | 1.64381 | 1.66140 | 1.64778 | 32.91 |
| 1.80 | 1.64610 | 1.66389 | 1.65007 | 32.69 |
| 2.00 | 1.64683 | 1.66474 | 1.65069 | 32.52 |
| 2.20 | 1.64609 | 1.66385 | 1.65008 | 32.73 |
| 2.40 | 1.64378 | 1.66137 | 1.64776 | 32.93 |
| 2.60 | 1.64001 | 1.65739 | 1.64395 | 33.12 |
| 2.80 | 1.63508 | 1.65176 | 1.63887 | 34.23 |
| 3.00 | 1.62807 | 1.64429 | 1.63177 | 34.82 |
| 3.20 | 1.61970 | 1.63496 | 1.62318 | 36.48 |
| 3.40 | 1.60920 | 1.62362 | 1.61250 | 37.94 |
| 3.60 | 1.59677 | 1.61029 | 1.59987 | 39.61 |
| 3.80 | 1.58243 | 1.59481 | 1.58528 | 42.18 |
| 3.85 | 1.57849 | 1.59063 | 1.58129 | 42.72 |
| 3.90 | 1.57413 | 1.58600 | 1.57687 | 43.37 |
| 3.95 | 1.56969 | 1.58121 | 1.57235 | 44.30 |

Figure 1:
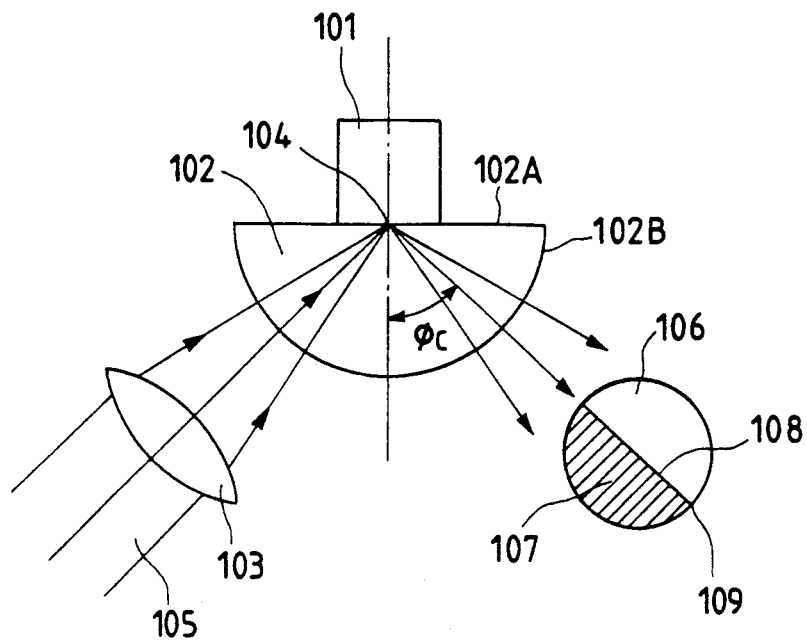
FIG. 1 is a sectional view illustrating the principle of the conventional optical system for measuring refractive index profiles.
Figure 3:
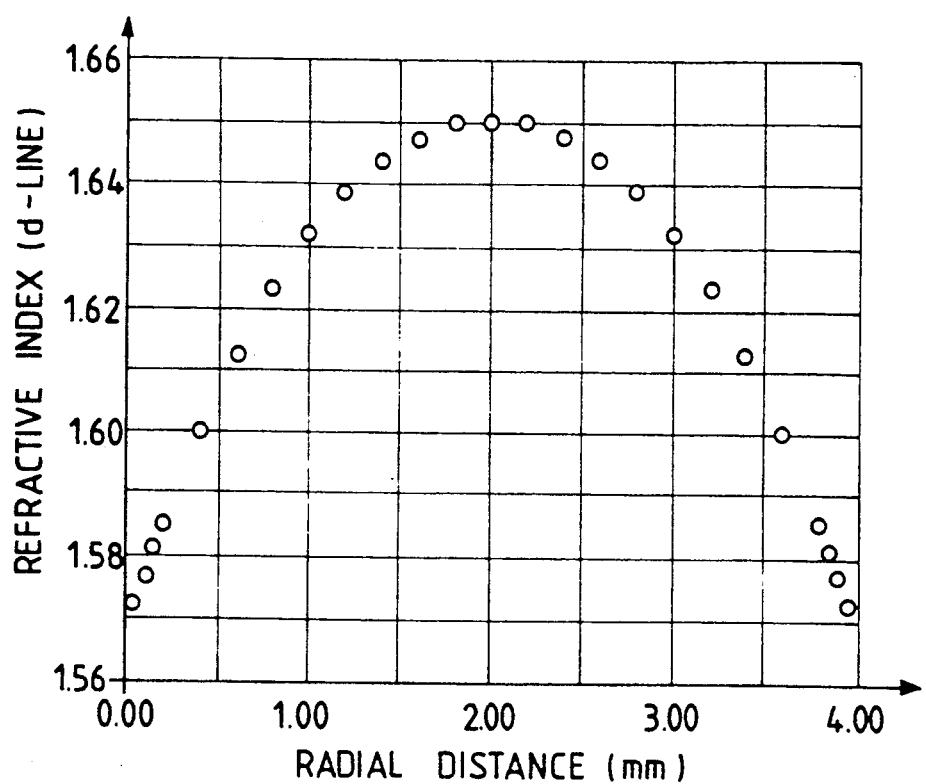
FIG. 3 is a diagram illustrating a refractive index profile at a main wavelength measured by the embodiment of the present invention shown in FIG. 2.
Figure 4:
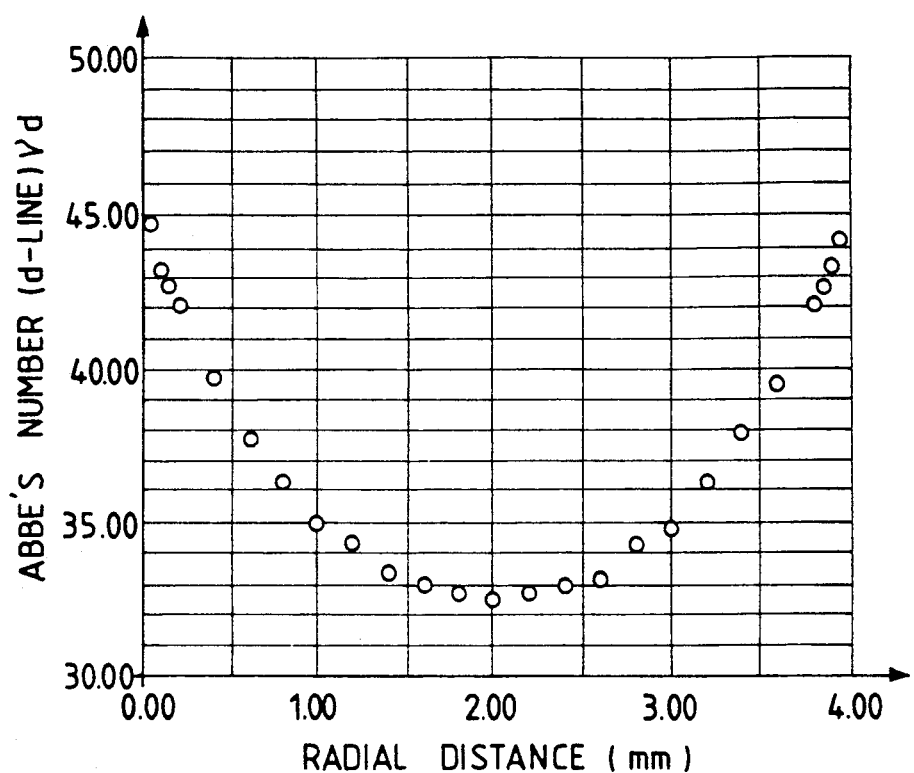
FIG. 4 is a diagram illustrating distributed dispersion at a main wavelength measured by the embodiment of the present invention shown in FIG. 2.
Figure 5:
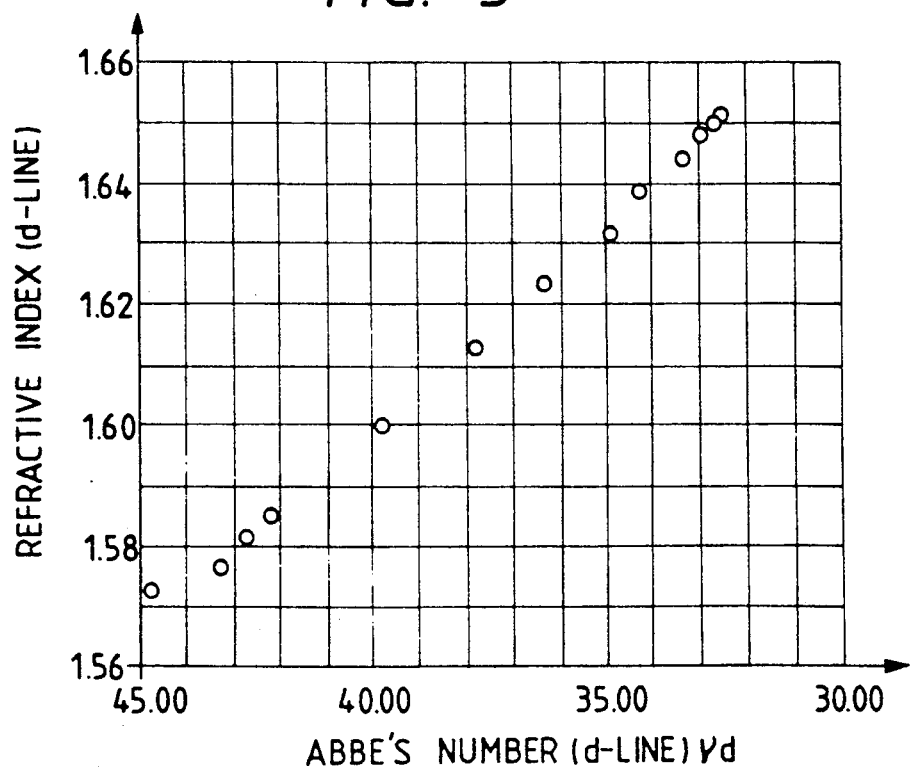
FIG. 5 is a diagram illustrating relationship between the refractive index profile and the distributed dispersion measured by the embodiment of the present invention shown in FIG. 2.

FIG. 3 illustrates a refractive index profile at the main wavelength (d-line, 587.56 nm) and FIG. 4 visualizes distributed dispersion at the main wavelength (d-line, 587.56 nm). A refractive index profile which is gradually lowered from a center in the diametrical direction and a distribution of Abbe's number which is progressively enhanced from the center in the diametrical direction were measured with high accuracies as is seen from FIG. 3 and FIG. 4 respectively. FIG. 5 shows relationship between refractive index and dispersion (Abbe's number) at the main wavelength which is generally selected by designers of optical systems to be used in the visible region (d-line, 587.56 nm). For facilitating understanding of the data, however, FIG. 5 shows data only within a range of one side of the hemispherical lens (within a range of 0.05 to 2.00 mm as measured from one edge of the hemispherical lens).

Since the embodiment illustrated in FIG. 2 adopts two light sources which emit laser beams having wavelength different from each other, this embodiment is effective only for measuring dispersion at a main wavelength and allows errors to be involved in measurements of samples exhibiting extraordinary dispersion. It is apparent, for measurements of samples exhibiting extraordinary dispersion, that dispersion including extraordinary dispersion can be measured accurately by using three or more light sources emitting light beams having wavelengths different from one another and accuracy of measurement can be enhanced by increasing the number of light sources emitting light beams to be used for the measurement.

In case where distributed dispersion including extraordinary dispersion is to be measured at an increased number of wavelengths by the method according to the present invention, no restrictive condition is posed on the optical system for carrying out the method, and it is sufficient for the measurements to add one or a plurality of light sources together with beam splitters and parallel plates in the optical system and along optical axes with one another. Further, it is possible for the purpose mentioned above to use an incoherent light source such as an Xe lamp together with a monochromator to prepare a monochromatic light beam or a light source emitting a spectral line. Though the photodetector is used as the measuring means 15 in the embodiment described above, it is possible to adopt an array of CCD's or a CCD camera in place of the photodetector or observe the reflected light beam by human eye.

Moreover, though the embodiment described above is configured so as to measure the critical angles of total reflection independently with the measuring point kept fixed after each scanning operation while alternately selecting, with the shutters 16 and 17, the laser beams emitted from the light sources, it is possible to measure the critical angles of total reflection at a plurality of wavelengths at the same time by adequately controlling intensities of the laser beams emitted from the light sources since the bright-dark boundaries are produced at the critical angles of total reflection which are different dependently on wavelengths of the laser beams emitted from the light sources even when the measuring point is irradiated simultaneously with the laser beams emitted from all the light sources.

Now, description will be made of an embodiment of the condenser optical system which is used for focusing the laser beams onto the measuring point 11 and has the alignment function.

Figure 6:
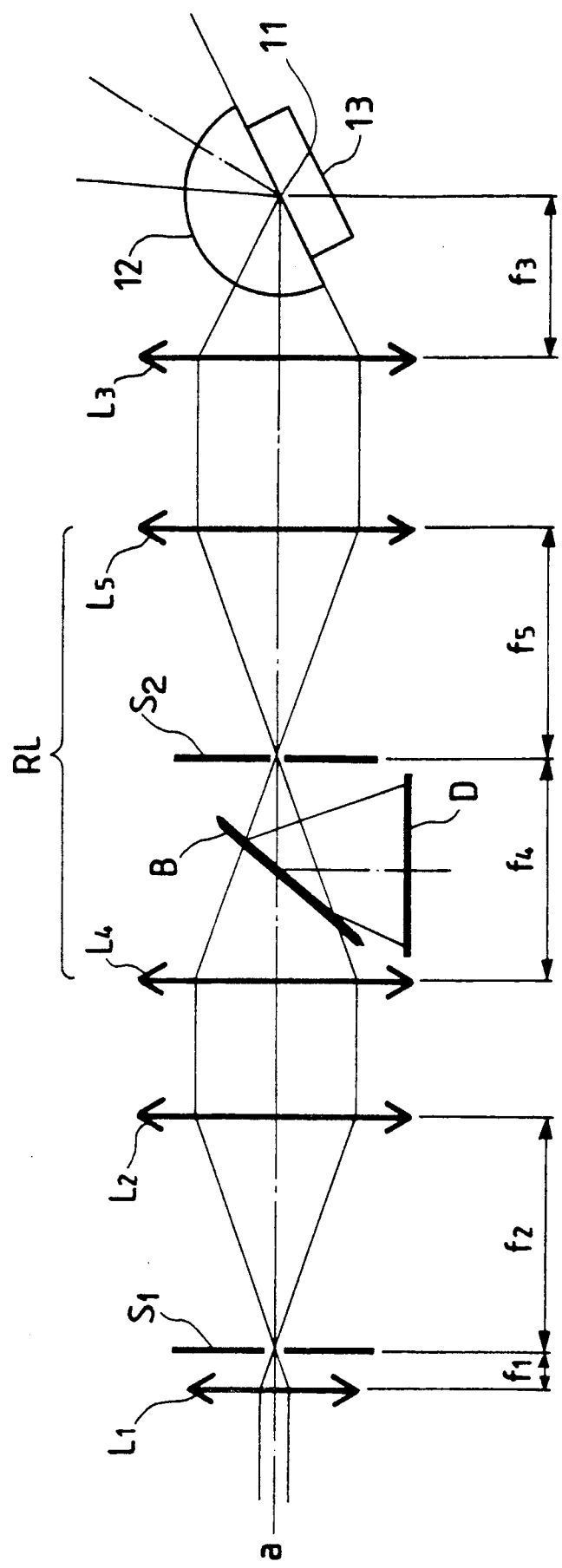
FIG. 6 is a sectional view illustrating a composition of an embodiment of the condenser optical system which is to be used in the optical system according to the present invention.

FIG. 6 illustrates the first embodiment of the condenser optical system. In FIG. 6, the reference symbol $L_1$ represents a lens which converges an incident light beam emitted from a light source, the reference symbol $S_1$ designates a stop which is disposed at a focal point of the lens $L_1$ and functions to shape a wave front of the light beam, the reference symbol $L_2$ denotes a collimator lens which makes a light beam having passed through the stop $S_1$ into a parallel light bundle, the reference symbol $L_3$ represents a condenser lens for condensing the light bundle onto the measuring point 11, and the reference symbol RL designates a relay lens system which is disposed between the collimator lens $L_2$, and the condenser lens $L_3$ for relaying the light bundle. The relay lens system consists of a first relay lens $L_4$ and a second relay lens $L_5$, and is designed as a lens system in which a rear focal point of the first relay lens $L_4$ is coincident with a front focal point of the second relay lens $L_5$. An alignment stop $S_2$ is disposed at the common focal point of the relay lenses $L_4$ and $L_5$. The reference symbol B represents a beam splitter which is disposed between the first relay lens $L_4$ and the alignment stop $S_2$, and the reference symbol D designates a photodetector means which is disposed in the optical path for the alignment light split by the beam splitter B for monitoring the alignment light beam. Disposed after the condenser lens $L_3$ is a hemispherical lens 12 which is selected as a medium member and arranged so that the light beam is focused onto the center of the sphere of the medium member. Further, placed on a flat bottom of the lens 12 is a sample 13 so that critical angle data obtained at the focused location of the light beam can be measured. In this optical system, a light bundle is focused by the condenser lens $L_3$ onto a center of the sphere of the lens 12 and a portion of the light bundle is reflected by the center of the sphere of the lens 12 so as to return to the original optical path as an aligned light beam.

Adopted to this condenser optical system are an objective lens which has a focal length of 9 mm and a magnification of 20× as the lens $L_1$, objective lenses which have a focal length of 36 mm and a magnification of 5× as the collimator lens $L_2$ and the relay lens $L_4$ respectively, and an objective lens which has a focal length of 72 mm and a magnification of 2.5× as the relay lens $L_5$. Each of these objective lenses has a parfocal distance of 45 mm. Used as the condenser lens $L_3$ is an objective lens having a focal length of 11 mm and a parfocal distance of 95 mm and a magnification of 10×. A pinhole having a diameter of 25 μm is used as the stop $S_1$ and a plurality of pinholes having diameters different from one another were selectively used in turn as the alignment stop $S_2$. The hemispherical lens 12 is made of a glass material which has a refractive index of 1.879 for a ray having a wavelength of 632.8 nm and an Abbe's number of 40.8. The hemispherical lens 12 has a diameter of 20 mm and surfaces which are polished with such high precision as to produce clear Newton's rings. The condenser optical system is designed so as to produce aberrations as little as possible.

The light beams are aligned as described below. First, the focusing point of the condenser optical system is roughly coincided with the center of the sphere of the lens 12 by an alignment mechanism provided on the lens 12 (not shown in FIG. 6). Then, the light beams emitted from the light sources 1 and 2 are focused onto the center of the sphere of the lens 12 by the condenser optical system. Portion of the light beams are reflected by the center of the sphere of the lens 12, travel through the condenser optical system in the reverse direction as aligned light beams and are split by the beam splitter B, and light intensities of the light beams are detected by the photodetector D. Precise alignment is performed by displacing the condenser lens $L_3$ along the optical axis and/or in the direction perpendicular to the optical axis.

Since the condenser optical system functions by using the stop $S_2$ as a positional standard for detecting the light beams reflected from the sample side, the condenser optical system is capable of performing the alignment more easily and with higher precision than an optical system which uses an ordinary automatic collimator, and exhibits a merit that the alignment is hardly influenced by vibrations, variations of temperature and so on. Further, since the stop $S_1$ for shaping a wave front and the stop $S_2$ for alignment are provided as separate members, the condenser optical system makes it possible to optimize sizes of the pinholes and perform the alignment with higher precision. In addition, the wave fronts of the incident light beams are disturbed and measurements may be adversely affected when the pinholes of the alignment stop $S_2$ have a small size. In such a case, the alignment stop $S_2$ should be removed out of the optical path after completing the alignment and before starting measurements.

Figure 7:
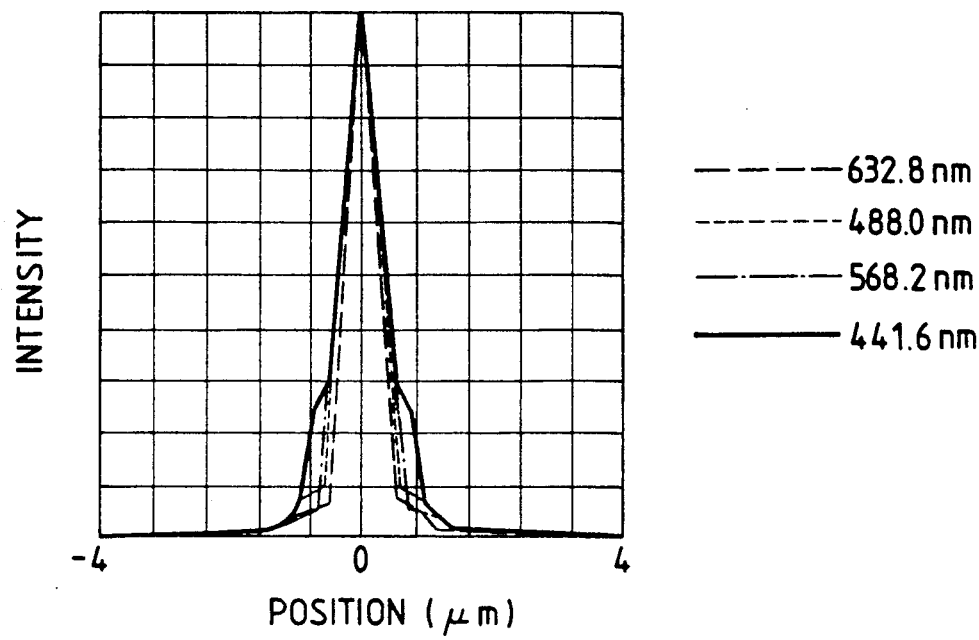
FIG. 7 shows graphs illustrating light intensity distributions on condensed beam spots which were obtained by simulations using the condenser optical system shown in FIG. 6.

Illustrated in FIG. 7 are results which were obtained by simulations using the embodiment shown in FIG. 6 of the condenser optical system. Used for these simulations were a laser source emitting an He-Ne laser having a wavelength of 632.8 nm, another laser source emitting an Ar laser having a wavelength of 488 nm, a third laser source emitting a Kr laser having a wavelength of 568.2 nm and a fourth laser source emitting an He-Cd laser having a wavelength of 441.6 nm. For the data illustrated in FIG. 7, laser beams having the wavelengths mentioned above were converged so as to have a diameter of 2 $\mu$m. Since the condenser optical system can converge the laser beams so as to have the diameter of 2 $\mu$m so far as chromatic aberration produced by the lenses are corrected completely and the laser beams are aligned with sufficiently high precision, the condenser optical system permits specifying a location of the measuring point with very high precision.

Figure 8:
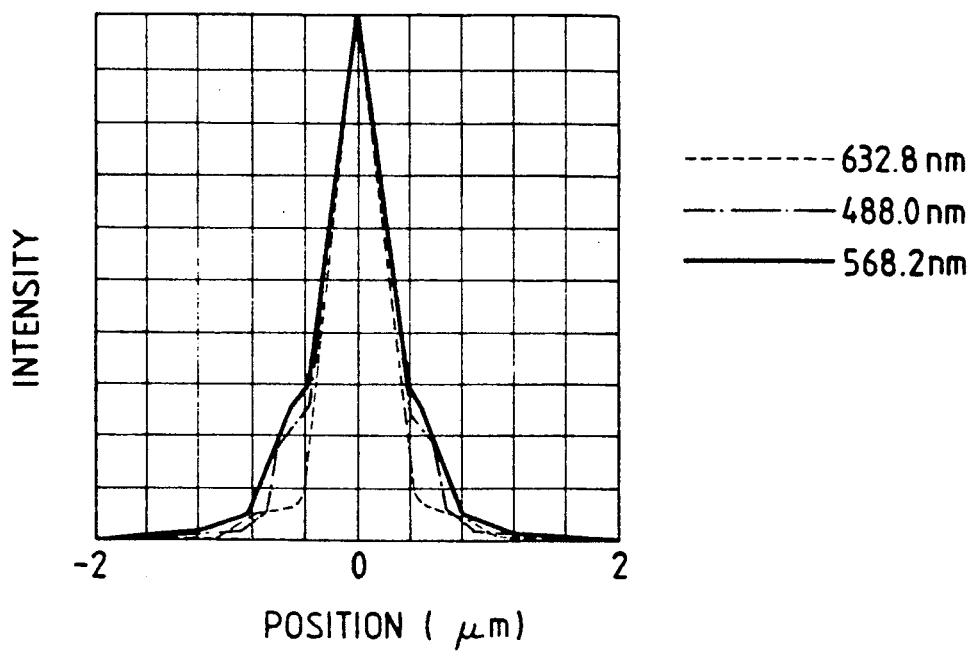
FIG. 8 shows graphs illustrating relationship light intensity distribution on condensed beam spots which were obtained by simulations using a condensing optical system which is slightly different from that shown in FIG. 6.

Even when a condensing optical system which has the composition shown in FIG. 6, the laser beams are focused on the measuring point at different degrees dependently on specifications for the condenser lens and so on. Let us assume, for example, that the lens $L_1$ is an objective lens which has a focal length of 3.6 mm and a magnification of 50×, the collimator lens $L_2$, the relay lens $L_4$ and the relay lens $L_5$ are objective lenses which have a focal length of 36 mm and a magnification of 5×, the condenser lens $L_3$ is an objective lens which has a focal length of 9 mm and a magnification of 20×, and each of the objective lenses has a parfocal distance of 45 mm in the condenser optical system. In this case, the stop $S_1$ has a pinhole having a diameter of 20 $\mu$m, and the beam splitter B has a size of a square of 10 mm × 10 mm and can be made of a glass material which has a refractive index of 1.515 at a wavelength of 632.8 nm and an Abbe's number of 64.2. Further, several types of alignment stops having pinholes 0.2 mm to 1 $\mu$m in diameter are prepared. These alignment stops are placed in the optical path selectively in an order from the ones having larger pinhole diameters to the others having smaller pinhole diameters. Though fine adjustment is performed by displacing the condenser lens $L_3$ in the embodiment shown in FIG. 6, the incident laser beams are located at the center of the sphere of the hemispherical lens 12 by displacing this hemispherical lens in the embodiment illustrated in FIG. 9. Light intensities of the focused laser beams which are aligned as described above are visualized in FIG. 8. Wavelengths of the laser beams used for obtaining the data are specified in FIG. 8. The laser beams having all the wavelengths are focused so as to form spots 2 $\mu$m in diameter. So far as chromatic aberration produced by the lenses are completely corrected, the condenser optical system focuses the laser beams to the degree described above and permits specifying locations of the measuring point with very high precision.

Figure 9:
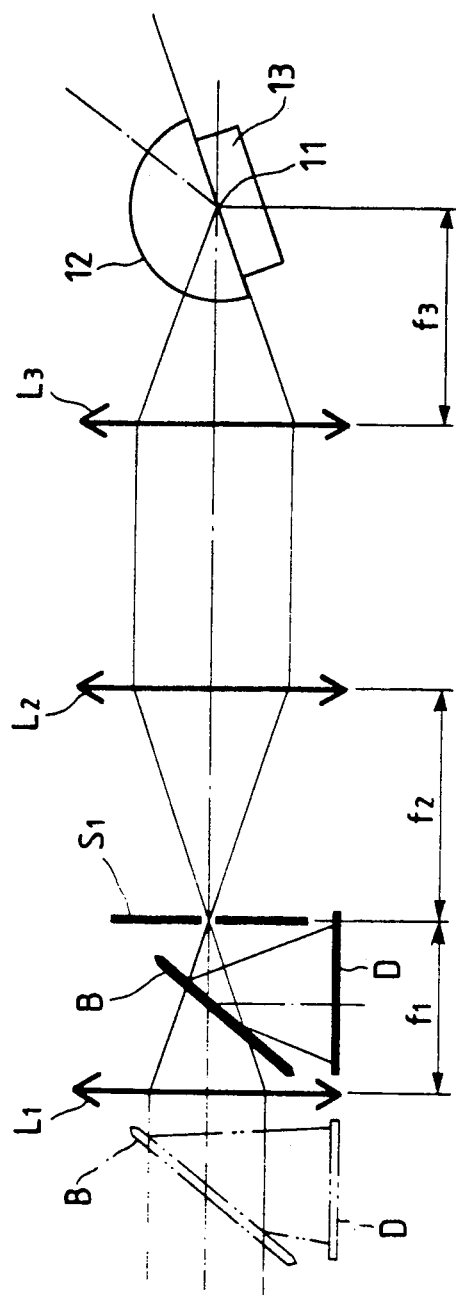
FIG. 9 is a sectional view illustrating a composition of a second embodiment of the condensing optical system to be used for carrying out the method according to the present invention.
Figure 10:
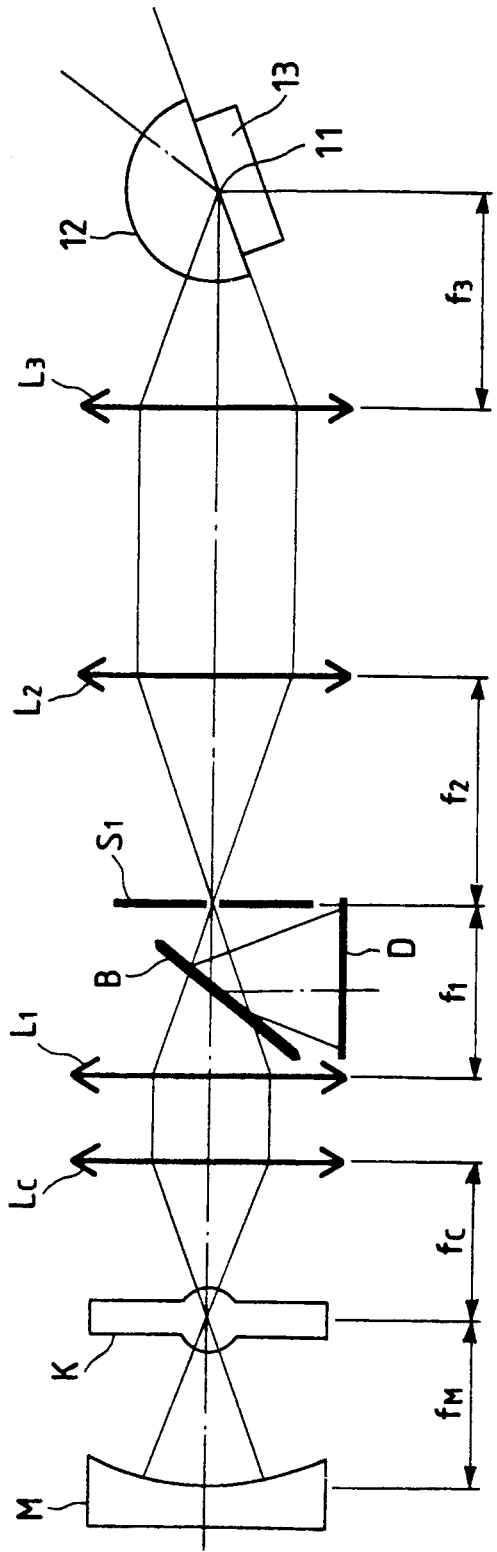
FIG. 10 is a sectional view illustrating a composition of a third embodiment of the condensing optical system to be used for carrying out the method according to the present invention.

The optical system disposed on the right side of the lens $L_2$ may be omitted when focusing degree of the laser beams need not be so high. FIG. 9 illustrates a condenser optical system which does not comprise the optical system arranged on the right side of the lens $L_2$. In case of the condenser optical system illustrated in FIG. 9, laser beams emitted from the light source are allowed to be incident on the lens $L_1$. In this case, the beam splitter B and the photodetector D may be disposed on the light source side of the lens $L_1$ as indicated by the chain lines. Further, an Hg-Xe lamp may be used as a light source through the light sources emitting lasers are adopted in the embodiments described above. FIG. 10 illustrates a third embodiment of the condenser optical system wherein an Hg-Xe lamp K is disposed. In this embodiment, disposed before and after (on the side of the lens $L_1$) the light source K are a concave mirror M and a synthetic quartz lens $L_c$ respectively so that light beams emitted from a front surface and a rear surface of the Hg-Xe lamp K are led as parallel light beams effectively into the condenser optical system. Further, disposed after the synthetic quartz lens $L_c$ are a lens $L_1$, a stop $S_1$ which is located at a focal point of the lens $L_1$, a collimator lens $L_3$ and a condenser lens $L_3$ in this order, and a sample 13 is placed at a location on which the light beams are focused. Arranged between the lens $L_1$ and the stop $S_1$ is a beam splitter B which splits aligned light beams reflected from the sample 13 so that the reflected light beams (aligned light beams) are led to a detector D. The third embodiment adopts a synthetic quartz lens having a focal length of 60 mm as the lens $L_1$, an objective lens which has a focal length of 36 mm and a magnification of 5× as the collimator lens $L_2$, an objective lens which has a focal length of 9 mm and a magnification of 20× as the condenser lens $L_3$, a pinhole having a diameter of 50 $\mu$m as the alignment stop $S_2$ and a beam splitter B made of a glass material which has a refractive index of 1.515 at a wavelength of 632.8 nm and an Abbe's number of 64.2 as the beam splitter B. Each of the objective lenses has a parfocal distance of 45 mm.

The concave mirror M has a focal length of 60 mm and the synthetic quartz lens $L_c$ has a focal length 60 mm.

In the third embodiment also, light intensities are detected with the detector D which consists of a lens (not shown) for condensing the aligned light beams reflected by the beam splitter B and a photodetector (not shown), and misalignment is reduced by using an alignment mechanism attached to the sample 13. In addition, the condenser optical system preferred as the third embodiment focuses the light beams onto a spot having a diameter of approximately 13 $\mu$m.

What is claimed is:
1. A method for measuring distributed dispersion of optical elements comprising:
   bringing a medium member having a refractive index higher than that of a sample into contact with one surface of the sample;
   allowing a plurality of light beams having wavelengths different from one another as incident light beams travelling along an optical axis to be focused on a measuring point on said surface through said medium member;

detecting bright-dark boundaries in reflected light beams having said wavelengths produced by total reflections on said measuring point as critical angles of total reflection;

determining refractive indices of said sample at said wavelengths from critical angles of total reflection at said wavelengths on said measuring point;

calculating dispersion of said sample at said measuring point from the refractive indices at said wavelengths; and determining distributed dispersion of said sample by repeating each of said steps while shifting said sample.

2. A method for measuring distributed dispersion of optical elements comprising:

bringing a medium member having a refractive index higher than that of a sample into contact with one surface of said sample;

allowing a plurality of light beams having wavelengths different from one another as converging light beams travelling along an optical path to be focused on a measuring point on said surface through said medium member;

detecting bright-dark boundaries in reflected light beams having said wavelengths produced by total reflections on said measuring point as critical angles of total reflection;

determining refractive indices of said sample at said wavelengths from critical angles of total reflection of the light beams having said wavelengths on said measuring point;

calculating a refractive index and dispersion of said sample for a light having a main wavelength from the refractive indices at said wavelengths; and determining a refractive index profile and distributed dispersion of said sample for the light having the main wavelength by repeating each of said steps while shifting said sample.

3. A distributed dispersion measuring device comprising:

light source means capable of emitting along one optical axis light beams having a plurality of wavelengths different from one another;

a collimator optical system making the light beams from said light source means into a parallel light bundle;

a substantially hemispherical sample supporting member transparent for the light beams from said light source means and having a flat surface on which a sample to be measured is placed;

a converging optical system for converging the parallel light bundle in the vicinity of a center of sphere of said sample supporting member;

a measuring means detecting the light beams reflected on said sample;

a means calculating dispersion of said sample at a measuring point on the basis of an output from said measuring means; and a scanning means moving said sample on the flat surface of said sample supporting member.

4. An optical system according to claim 3 wherein said collimator optical system comprises a converging optical component, a stop disposed on an optical axis of light beams having passed through said converging optical component, a collimator optical component for transforming light beams having passed through said stop into parallel light beams, a light beam splitter means disposed on the incidence side of said stop and functioning to split rays reflected by spherical surface of said sample supporting member, and a photodetector disposed on an optical axis of light beams split by said light beam splitter means.

5. An optical system according to claim 3 wherein said collimator optical system comprises:

a converging optical component, a stop disposed on an optical axis of light beams having passed through said converging optical component, a collimator optical component for transforming light beams having passed through said stop into parallel light beams, a relay lens system including a first lens system for converging the parallel light beams having passed through said collimator optical component and a second lens system disposed so as to have a focal point coincident with that of said first lens system, a stop for alignment disposed at the common focal point of said first lens system and said second lens system, a light beam splitter means disposed on the incidence side of said stop for alignment, and functioning to split light beams reflected and returned by a spherical surface of said sample supporting member, and a photodetector disposed on an optical axis of light beams split by said light beam splitter means.

* * * * *